United States Patent [19]

Adelstein et al.

[11] 4,013,668

[45] Mar. 22, 1977

[54] 5-(1,1-DIPHENYL-3-(5- OR 6-HYDROXY-2-AZABICYCLO(2.2.2)OCT-2-YL)PROPYL)-2-ALKYL-1,3,4-OXADIAZOLES AND RELATED COMPOUNDS

[75] Inventors: Gilbert W. Adelstein, Evanston; Aziz Karim, Niles; Chung H. Yen, Skokie, all of Ill.

[73] Assignee: G. D. Searle & Co., Chicago, Ill.

[22] Filed: Mar. 10, 1976

[21] Appl. No.: 665,609

[52] U.S. Cl. .......................... 260/293.54; 424/267
[51] Int. Cl.² ....................................... C07D 413/06
[58] Field of Search ........................... 260/293.54

[56] References Cited

UNITED STATES PATENTS 3,917,615  11/1975  Adelstein ..................... 260/293.54

*Primary Examiner*—G. Thomas Todd
*Attorney, Agent, or Firm*—John J. Kolano

[57] ABSTRACT

This invention encompasses novel 5-[1,1-diphenyl-3-(5-or 6-hydroxy-2-azabicyclo[2.2.2]oct-2-yl)propyl]-2-alkyl-1,3,4-oxadiazoles and their lower O-alkanoyl derivatives. These compounds are useful anti-diarrheal agents and also possess little or no analgesic activity.

10 Claims, No Drawings

5-(1,1-DIPHENYL-3-(5- OR 6-HYDROXY-2-AZABICYCLO(2.2.2)OCT-2-YL)PROPYL)-2-ALKYL-1,3,4-OXADIAZOLES AND RELATED COMPOUNDS

The present invention is concerned with 5-[1,1-diphenyl-3(5-or 6-hydroxy-2-azabicyclo[2.2.2]oct-2-yl) propyl]-2-alkyl-1,3,4-oxadiazoles and their lower O-alkanoyl derivatives. More particularly, this invention is concerned with compounds of the formula

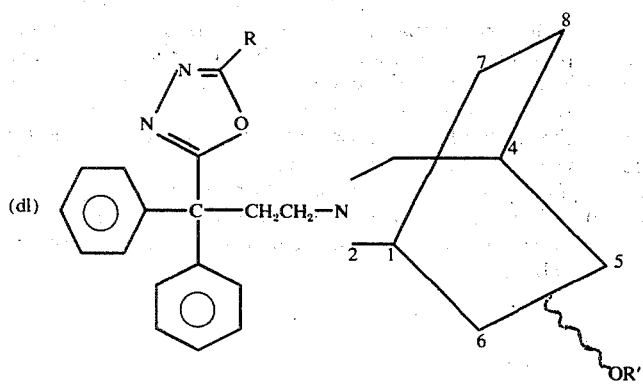

wherein R is lower alkyl containing from 1 to 6 carbon atoms; R' is hydrogen or lower alkanoyl containing from 2 to 7 carbon atoms; and OR' is attached at the 5- or 6-position in either the endo or exo configuration.

Particularly preferred compounds of this invention are those of the formula

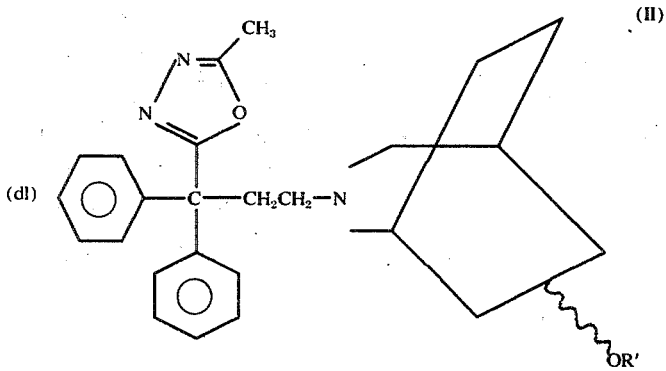

wherein R' is hydrogen or acetyl and —OR' at the 5- or 6-position is in either the endo or exo configuration.

The lower alkyl radicals referred to above contain 1 to 6 carbon atoms and are exemplified by methyl, ethyl, propyl, butyl, pentyl, hexyl and the corresponding branched chain isomers thereof. The lower alkanoyl radicals contain 2 to 7 carbon atoms and are typified by acetyl, propionyl, butyryl and the like.

Equivalent to the compounds of formulas (I) and (II) for the purposes of the invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

The compounds of the present invention are useful in consequence of their valuable pharmacological properties. They are, for example, potent anti-diarrheal agents as evidenced by their ability to inhibit gastrointestinal motility as set out in the following tests.

CHARCOAL MEAL TEST

The method used for this assay is a modification of the techniques previously described by Macht and Barba-Gose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration the animals are sacrificed and the cecum examined for the absence or presence of charcoal on an all-or-none basis.

The median effective dose ($ED_{50}$) is then calculated for each compound using the logistic method of Berkson (1953).

CASTOR OIL-INDUCED DIARRHEA IN THE RAT

Adult Charles River male rats are fasted in community cages for 24 hours prior to the test with free access to water. The test compound is then administered intragastrically (suspended in 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

In addition to their anti-diarrheal activity, the compounds of this invention demonstrate little or no analgesic activity at the test doses. The assessment of this activity is conducted by the following assay:

TAIL CLIP TEST

A special clip is applied to the base of the tail of an adult male mouse weighing 18–25 grams and the time for the animal to turn around to bite at the clip is measured. The sensitivity of each mouse is determined ½ hour prior to drug administration and only those mice attempting to bite the clip are included in the experiment. The test compound is the administered intraperitoneally and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

A representative compound of this invention which is particularly active in the Charcoal Meal Test anti-diarrheal assay and which possesses no analgesic activity is 5-[1,1-diphenyl-3-(exo-5-hydroxy-2-azabicyclo[2.2.2]oct-2-yl)-propyl]-2-methyl-1,3,4-oxadiazole.

The compounds of formula (I) may be combined with various pharmaceutical carriers to provide compositions suitable for use in the treatment of diarrhea. The dosage of these compounds is dependent upon various factors such as the compound employed and the particular response obtained. Typical dosages for use as an anti-diarrheal agent vary from 0.1 to 25 mg./kg. per day administered orally.

The compounds of the present invention are conveniently prepared by the reaction sequence set out in Scheme A.

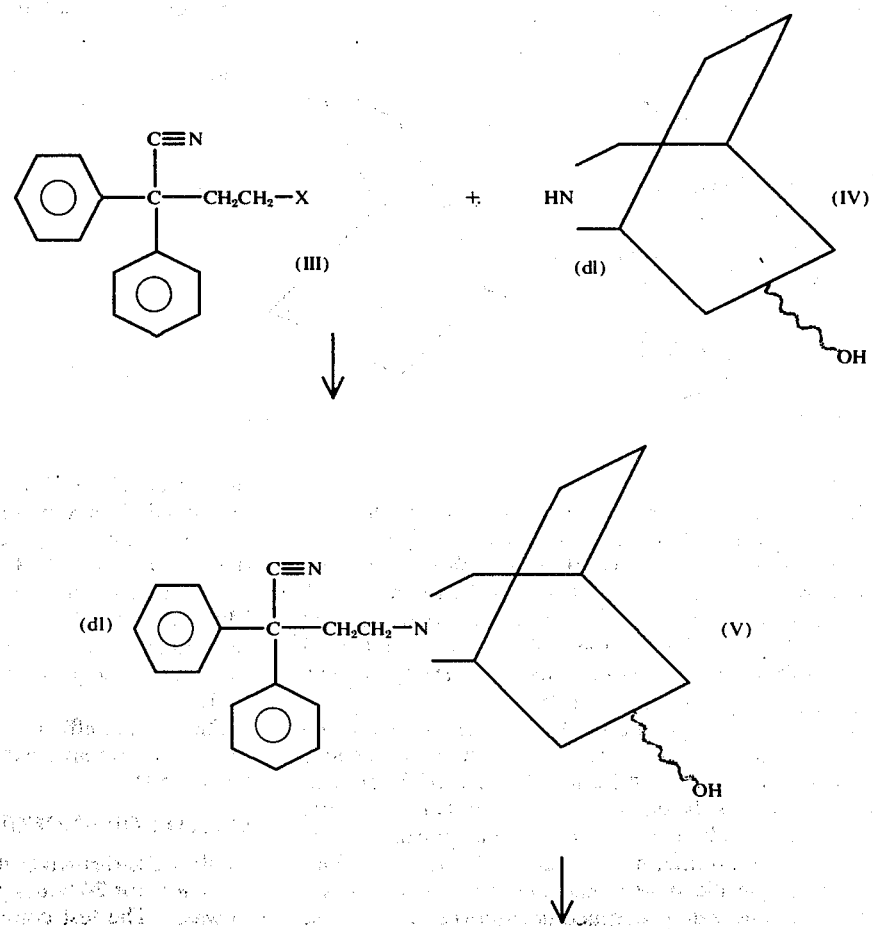

Scheme A

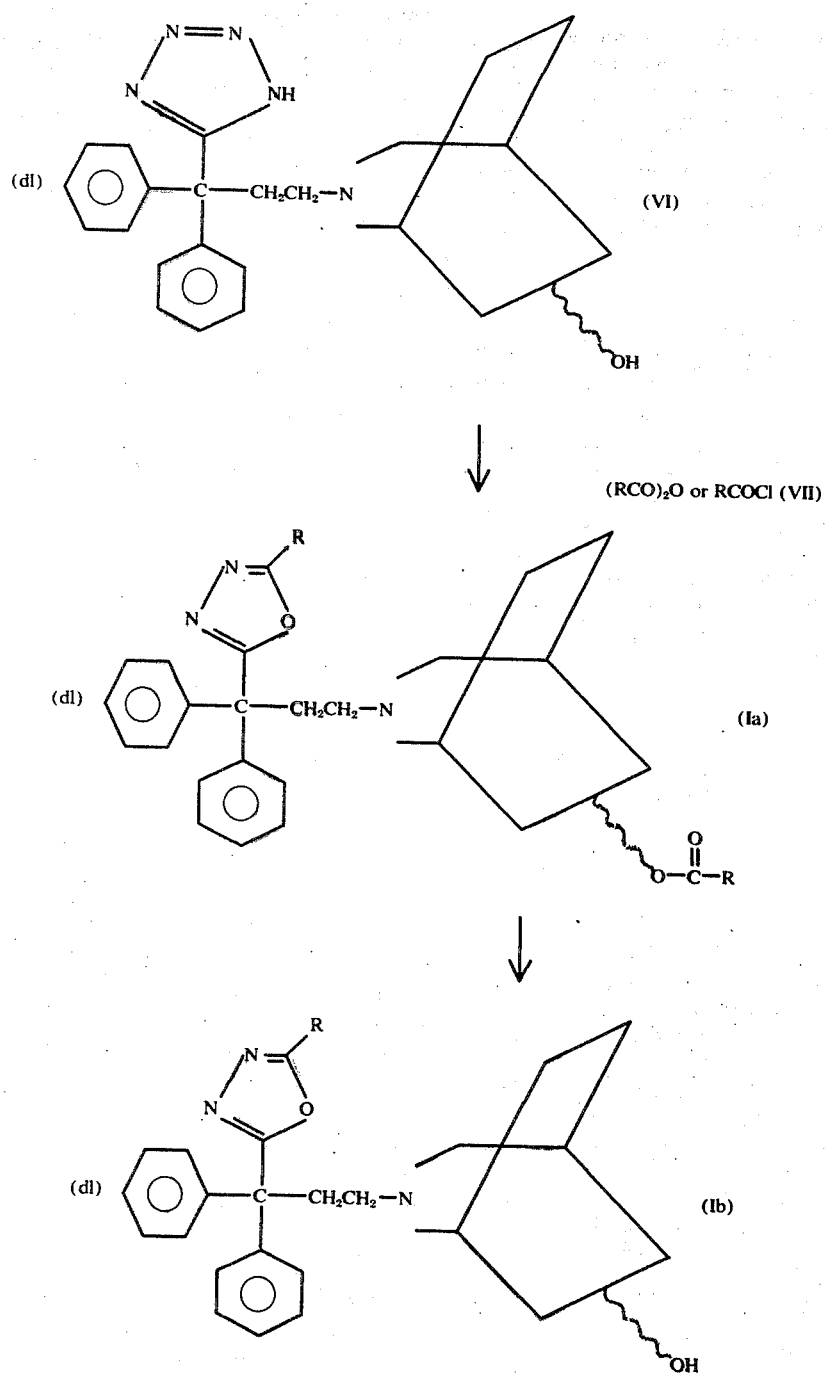

As illustrated in Scheme A, the secondary amine of formula (IV) is reacted with an alkyl halide of formula (III) wherein the X represents an iodo, bromo or chloro atom to form the nitrile of formula (V). This reaction is preferably, but not absolutely, carried out in an organic solvent. An alkylation promoter, such as sodium iodide or potassium iodide, and an acid acceptor, such as potassium carbonate, may optionally be added to facilitate the reaction. Suitable organic solvents are those such as benzene, toluene, and methylene chloride, with a particularly preferred solvent being methyl isobutyl ketone.

The nitrile of formula (V) is then reacted with an azide ion by methods similar to those described by Moersch and Morrow, J. Med. Chem., 10, 149 (1967) to obtain the tetrazole of formula (VI).

The tetrazoles of formula (VI) are converted to the compounds of formula (I) wherein R' is a lower alkanoyl radical containing 2 to 7 carbon atoms, i.e., the compounds illustrated in the above scheme by formula (Ia) by reaction with an appropriate acylating agent of formula (VII) wherein R is defined as hereinbefore. This reaction is conveniently conducted in an organic solvent, with a particularly preferred solvent being pyridine.

Alkaline hydrolysis of the compounds of formula (Ia) with a suitable reagent such as sodium hydroxide affords the compounds of formula (I) wherein R' is hydrogen, i.e., the compounds illustrated in the above Scheme A by formula (1b).

The following examples describe in detail the preparation of compounds of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

15.5 Parts of methyl 2-hydroxy-4-aminobenzoate is dissolved in approximately 180 parts of ethanol. Then, 3.89 parts of a 5% rhodium-on-alumina catalyst is added and the mixture shaken at 60° C. at a pressure of about 60 psi for approximately 53 hours. The catalyst is removed by filtration and the filtrate concentrated under reduced pressure. The residual oil which solidifies upon standing is triturated with 60 parts by volume of a 4:1 ether-ethanol mixture, filtered, washed with 100 parts by volume of a 4:1 ether-ethanol mixture, and dried in vacuo to give methyl 2-cis-hydroxy-4-cis-aminocyclohexanecarboxylate acetate. This compound melts at about 134°–137° C., and is represented by the following structural formula.

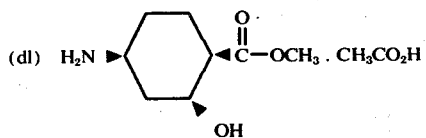

EXAMPLE 2

44.5 Parts of methyl 2-cis-hydroxy-4-cis-aminocyclohexanecarboxylate acetate is heated at about 160°–165° C. for about 3.5 hours under a nitrogen atmosphere. The gas which evolves during heating is condensed by cooling and collected. The residual solid is, after cooling, triturated with 20 parts methanol, cooled to 0° C., filtered, washed with methanol and ether, and air-dried. The resultant off-white solid is recrystallized from methanol to give exo-5-hydroxy-2-azabicyclo-[2.2.2]octan-3-one, melting at about 263°–266° C., and represented by the following structural formula.

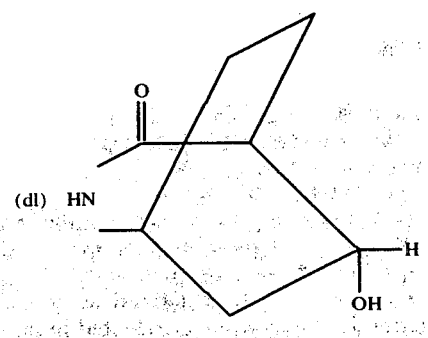

EXAMPLE 3

To a suspension of 27.9 parts lithium aluminum hydride in 2500 parts dry ethyl ether under nitrogen is added 34.3 parts of exo-5-hydroxy-2-azabicyclo[2.2.2]octan-3-one. The resulting mixture is refluxed for 23 hours with stirring. The reaction is then decomposed by the successive addition of 29.4 parts water, 22 parts by volume of a 20% sodium hydroxide solution, and 108 parts water. The solution is then filtered, the inorganic salts washed with ethyl ether and the filtrates combined. These combined filtrates are then treated with a slight excess of a solution of hydrochloric acid in isopropanol. Removal of the solvents in vacuo affords a solid residue which is triturated with 32 parts acetone, filtered, washed, and air-dried to afford an off-white solid. Recrystallization of this solid from a mixture of acetone and methanol affords exo-2-azabicyclo[2.2.2]octan-5-ol hydrochloride. This compound melts at about 308°–310° C. with decomposition and is represented by the following structural formula.

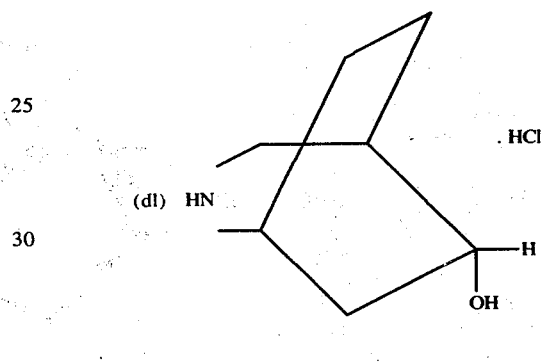

EXAMPLE 4

16.3 Parts of exo-2-azabicyclo[2.2.2]oct-5-ol hydrochloride is dissolved in 67 parts of hot ethanol. After cooling the solution to room temperature a solution of 4.0 parts sodium hydroxide in 67 parts ethanol is added. The resulting precipitate is filtered off and washed with 32 parts ethanol. The filtrates are combined, mixed with 13.8 parts of potassium carbonate and 12.7 parts benzyl chloride, and heated to reflux for about 4 hours under a nitrogen atmosphere. After cooling, the solvents are removed in vacuo and the residue suspended in 140 parts by volume of a potassium carbonate solution which was saturated with sodium chloride. This suspension is extracted twice with ethyl ether. The ether extracts are then combined and twice extracted with dilute hydrochloric acid. These extracts are combined and basified with aqueous sodium hydroxide. The resulting liberated oil is separated by twice extracting with ether and combining the ether extracts which are then dried over anhydrous sodium sulfate and stripped of solvent in vacuo. The residual oil is dissolved in 39 parts acetone, treated with 15 parts by volume of a 7.3 N solution of hydrochloric acid in isopropanol and cooled in a cold-water bath. The resulting precipitate is filtered, washed with acetone and air-dried to give exo-2-benzyl-2-azabicyclo[2.2.2]octan-5-ol hydrochloride. This compound melts at about 157°–160° C. and is represented by the following structural formula.

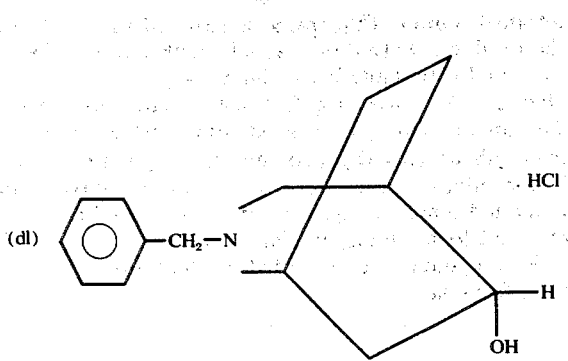

EXAMPLE 5

7.83 Parts of exo-2-benzyl-2-azabicyclo[2.2.2]octan-5-ol hydrochloride is dissolved in 1200 parts boiling acetone. The hot solution is filtered and the volume reduced to about 450 ml. After cooling to about 15° C., 11.6 parts by volume of an 8 N Jones reagent is added and the solution stirred for about 2.5 hours. An additional 51.4 parts by volume Jones reagent is then added with the temperature being kept at 33° C. by means of a cold-water bath. After stirring for an additional 16 hours at room temperature, the solution is quenched with 75 parts by volume isopropanol, treated with 21 parts of potassium carbonate in 150 parts water and reduced in volume in vacuo to about 200 ml. The resulting green slurry is then treated with a solution of 21 parts potassium carbonate in 350 parts water and extracted with ethyl ether. The ether extracts are combined, dried over anhydrous sodium sulfate and stripped in vacuo to yield a yellow oil. This oil is dissolved in 24 parts acetone and treated with 3.5 parts by volume of a 7.25 N solution of hydrogen chloride in isopropanol, with cooling. The resulting white crystals are filtered, washed with acetone and dried under vacuum to afford 2-benzyl-2-azabicyclo[2.2.2]-octan-5-one hydrochloride. This compound melts at about 153°–154° C. and is represented by the following structural formula.

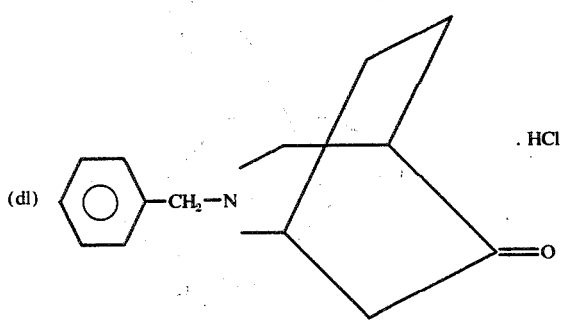

EXAMPLE 6

A solution of 3.77 parts 2-benzyl-2-azabicyclo[2.2.2]-octan-5-one in water is basified using aqueous sodium hydroxide. The liberated oil is separated by extracting with benzene, combining the extracts, drying the extracts over anhydrous sodium sulfate and anhydrous potassium carbonate and removing the solvent in vacuo. The residual oil is then redissolved in benzene and the solvent removed in vacuo. To the residual oil dissolved in 45 parts dry tetrahydrofuran is added dropwise with stirring 39 parts by volume of a 1.17 M solution of diisobutyl aluminum hydride in toluene over a period of 70 minutes under nitrogen at −70° C. Stirring at this temperature is continued for an additional 4 hours. The mixture is allowed to warm to room temperature and left to stir for a further 16 hours. After cooling to about 0°–5° C., the reaction mixture is decomposed with 16 parts methanol. The solvents are then removed in vacuo to leave a thick oil which is dissolved in methylene chloride, washed with sodium hydroxide, dried over anhydrous sodium sulfate and stripped in vacuo. Gas chromatography of the remaining oil shows a 6:4 mixture of endo-2-benzyl-2-azabicyclo[2.2.2]octan-5-ol and exo-2-benzyl-2-azabicyclo[2.2.2]octan-5-ol.

This mixture is treated with a solution of hydrochloric acid in isopropanol to form the hydrochloride salt. Fractional crystallization of this salt from a 1:10 (v/v) mixture of methanol-acetone affords 98% pure endo-2-benzyl-2-azabicyclo[2.2.2]octan-5-ol hydrochloride, melting at about 189°–192° C.

EXAMPLE 7

0.52 Part of endo-2-benzyl-2-azabicyclo[2.2.2]octan-5-ol is dissolved in approximately 40 parts of ethanol. Then, 0.05 part of a 5% palladium-on-carbon catalyst is added and the mixture shaken at room temperature and at a pressure of about 60 psi for approximately 18.5 hours. The catalyst is removed by filtration and the solvents removed in vacuo. The residual solid is triturated with 18 parts of dry ether, and filtered off and air-dried at 60° C. Recrystallization of the solid from a mixture of methanol and tetrahydrofuran affords endo-2-azabicyclo[2.2.2]octan-5-ol hydrochloride, melting at about 310°–312° C. with decomposition and gas evolution. This compound is represented by the following structural formula.

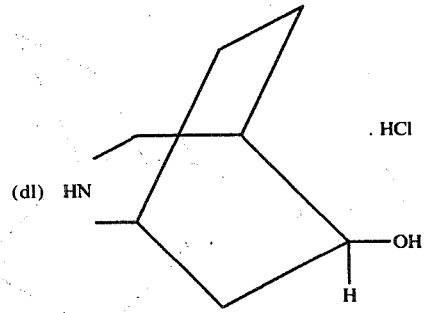

EXAMPLE 8

141 Parts of m-chloroperbenzoic acid is added portionwise to a stirred solution of 90.0 parts methyl 3-cyclohexene-1-carboxylate in 2200 parts chloroform over a 20 minute period at -4 - 1° C. The resultant solid suspension is stirred at room temperature for 70 minutes. The solid is separated by filtration and washed with chloroform. The filtrate and the washing are combined, washed successively with dilute sodium sulfate, dilute sodium bicarbonate and water, dried over anhydrous sodium sulfate, and stripped in vacuo. The residual oil is distilled to afford, as a colorless liquid boiling at 57° C. at 0.6 mm. to 66° C. at 0.8 mm. pressure, a mixture of cis and trans methyl 3,4-epoxycyclohexane- 1-carboxylate. This mixture is represented by the following structural formulas.

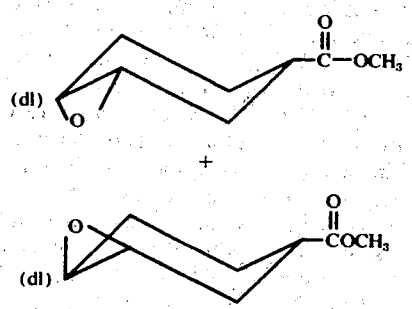

EXAMPLE 9

A solution of 99.3 parts of the mixture of cis and trans methyl 3,4-epoxycyclohexane-1-carboxylate and 71.5 parts benzylamine in 240 parts ethanol is refluxed for 18 hours, then cooled, and stripped of solvent in vacuo. The residue is then refluxed with 320 parts methanol and 405 parts by volume of a 10% potassium hydroxide solution for 1 hour. After cooling, the solution is neutralized to a pH of 7 with dilute hydrochloric acid and then stripped in vacuo to a volume of 550 ml. The resultant solid suspension is filtered and the solid washed with water and air-dried. This solid is heated for about 45 minutes at 215°–225° C. which results in the solid melting with water vapor evolution. After cooling, the residue is dissolved in methylene chloride, washed successively with dilute hydrochloric acid, water, dilute potassium carbonate and water, then dried over anhydrous sodium sulfate and stripped in vacuo. The residue is crystallized from ethyl acetate to afford endo-2-benzyl-6-hydroxy-2-azabicyclo[2.2.2]-octan-3-one, melting at 96.5°–99° C., and represented by the following structural formula.

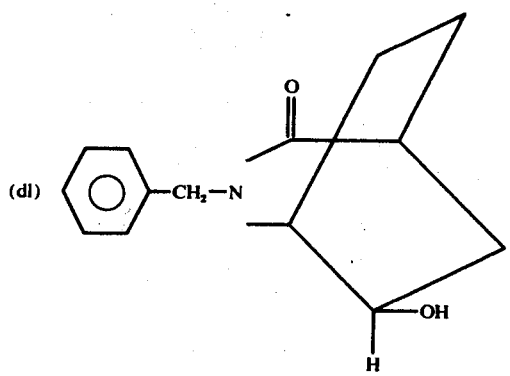

EXAMPLE 10

To a suspension of 26.0 parts lithium aluminum hydride in 670 parts tetrahydrofuran under nitrogen at reflux is added with stirring a suspension of 43.0 parts endo-2-benzyl-6-hydroxy-2-azabicyclo[2.2.2]octan-3-one in 130 parts tetrahydrofuran over a 20 minute period. After refluxing the reaction mixture for about 64 hours, the mixture is decomposed by the successive addition of 27.4 parts water, 20.6 parts by volume of a 20% sodium hydroxide solution and 96 parts water. The solid is removed by filtration and washed with tetrahydrofuran. The filtrate is stripped in vacuo and the residue dissolved in ether. The ethereal solution is extracted with dilute hydrochloric acid and the hydrochloric acid extract basified with sodium hydroxide. The liberated oil is extracted into ethyl ether, dried over anhydrous sodium sulfate and stripped in vacuo. The residual solid is recrystallized from a mixture of ether and n-hexane to afford endo-2-benzyl-2-azabicyclo[2.2.2]octan-6-ol, melting at about 77°–78.5° C. This compound is represented by the following structural formula.

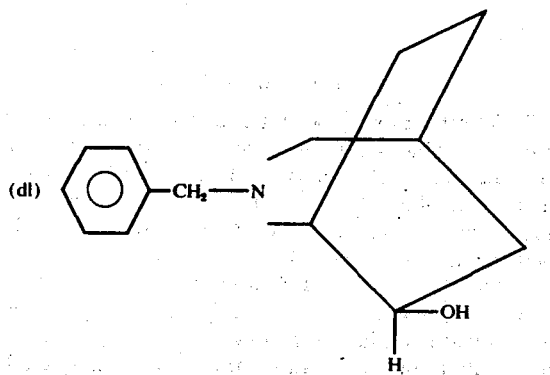

EXAMPLE 11

18.0 Parts of endo-2-benzyl-2-azabicyclo[2.2.2]octan-6-ol is dissolved in approximately 200 parts ethanol. Then, 1.8 parts of a 5% palladium-on-carbon catalyst is added and the mixture shaken at room temperature and at a pressure of 36–60 psi for approximately 6 hours. The catalyst is removed by filtration and the filtrate concentrated under reduced pressure to afford a white solid. Recrystallization from a mixture of methylene chloride and n-hexane yields endo-2-azabicyclo[2.2.2]-octan-6-ol melting at about 220°–224° C. This compound is represented by the following structural formula.

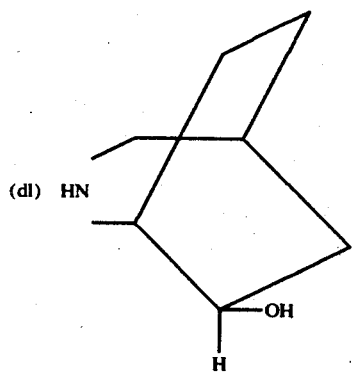

EXAMPLE 12

A solution of 34.0 parts endo-2-benzyl-2-azabicyclo[2.2.2]octan-6-ol in 106 parts hot acetone is cooled in an icewater bath and treated with a slight excess of hydrochloric acid in isopropanol. Cooling to 0° C. and seeding results in a precipitate which is filtered, washed with acetone and air-dried to afford endo-2-benzyl-2-azabicyclo[2.2.2]octan-6-ol hydrochloride. This compound melts at about 174°–175° C. and is represented by the following structural formula.

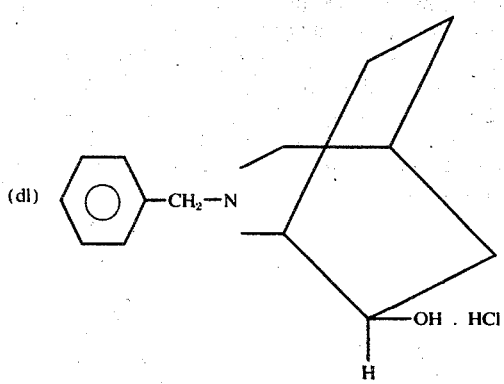

EXAMPLE 13

To a solution of 37.7 parts endo-2-benzyl-2-azabicyclo[2.2.2]octan-6-ol hydrochloride in 790 parts acetone is added with stirring, 500 parts by volume of an 8 N solution of Jones reagent over a 20 minute period at 20°–30° C. After stirring at about 15°–20° C. for 2 hours the temperature is reduced to 0°–5° C., and the solution stirred thereat for an additional 18 hours. Then, the reaction mixture is decomposed by the addition of 240 parts isopropanol and poured into 1000 parts by volume of an ice-cold 6 N sodium hydroxide solution. The solution is saturated with sodium chloride and extracted three times with 710 parts ethyl ether. The ether extracts are combined, dried over anhydrous sodium sulfate and stripped in vacuo. The residue is partitioned between water and ether. The ether layer is separated, dried over sodium sulfate and stripped in vacuo to afford a brown oil. Distillation of this oil affords the desired 2-benzyl-2-azabicyclo[2.2.2]octan-6-one, boiling at 126°–141° C. at 0.1 mm. pressure.

Treatment of the above oil with a solution of hydrogen chloride and isopropanol affords the corresponding salt, 2-benzyl-2-azabicyclo[2.2.2]octan-6-one hydrochloride, as white crystals. This compound melts at about 215°–216° C., and is represented by the following structural formula.

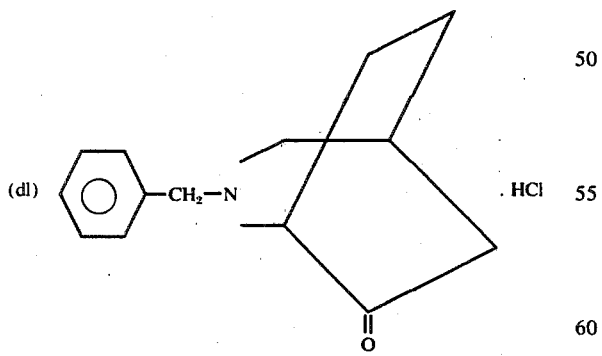

EXAMPLE 14

11.7 Parts 2-benzyl-2-azabicyclo[2.2.2]octan-6-one hydrochloride is suspended in 110 parts water and 13.8 parts potassium borohydride is added under nitrogen. After stirring overnight, the resulting two phases are extracted with ether. The ether extract is dried over anhydrous sodium sulfate and stripped in vacuo to give, as a light yellow oil, a 32:67 mixture of endo-2-benzyl-2-azabicyclo[2.2.2]octan-6-ol and exo-2-benzyl-2-azabicyclo[2.2.2]octan-6-ol.

This mixture is separated by low pressure chromatography using a neutral alumina column and increasing amounts of ethyl acetate in methylene chloride as eluant. The fractions eluded with 100% methylene chloride are combined, stripped in vacuo and the residue dissolved in ether. The ethereal solution is filtered and treated with a solution of hydrogen chloride in isopropanol. The white precipitate is filtered, and air-dried, to afford exo-2-benzyl-2-azabicyclo[2.2.2]octan-6-ol hydrochloride, melting at 210°–203° C. This compound is represented by the following structural formula.

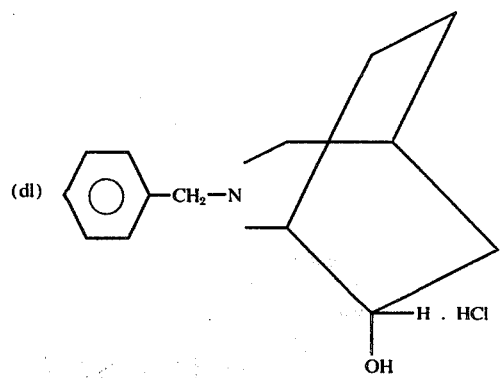

EXAMPLE 15

Repetition of the procedure of Example 11 using exo-2-benzyl-2-azabicyclo[2.2.2]octan-6-ol affords exo-2-azabicyclo[2.2.2]octan-6-ol. This compound is represented by the following structural formula.

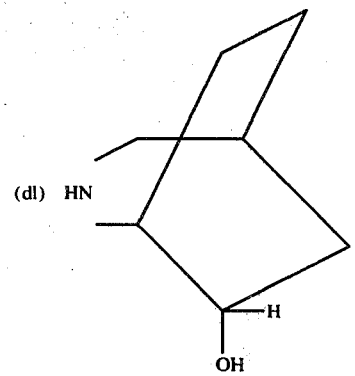

EXAMPLE 16

To a solution of 2.46 parts exo-2-azabicyclo[2.2.2]octan-5-ol hydrochloride in 10 parts water is added 3.32 parts potassium carbonate and 2.25 parts sodium iodide. Then, 4.80 parts 2,2-diphenyl-4-bromobutyronitrile and 120 parts methyl isobutyl ketone is added and the mixture heated to reflux, with stirring. After refluxing for 18 hours, the reaction mixture is cooled to room temperature and the solvents removed in vacuo. The residue is partitioned between ethyl ether and dilute sodium hydroxide. The ethereal layer is separated and extracted with dilute hydrochloric acid. This results in the formation of a solid precipitate. The ethereal layer and the solid precipitate are extracted with water and this water extract combined with the dilute hydrochloric acid extract. These combined extracts are basified with aqueous sodium hydroxide to liberate an oil. The oil is extracted into an ether layer which is then washed three times with water, dried successively over anhydrous sodium sulfate and anhydrous potassium carbonate and treated with excess hydrogen chloride in isopropanol solution. The precipitate which results is filtered, air-dried and recrystallized from a mixture of ethanol and ether to afford 2,2-diphenyl-4-(exo-5-hydroxy-2-azabicyclo[2.2.2]oct-2-yl)-butyronitrile hydrochloride. This compound melts at about 245°–247° C.

Treatment of the above hydrochloride salt with aqueous sodium hydroxide, followed by extraction into ethyl ether and stripping of the solvents in vacuo affords the free base, 2,2-diphenyl-4-(exo-5-hydroxy-2-azabicyclo[2.2.2]oct-2-yl)butyronitrile. This compound is represented by the following structural formula.

0.51 parts sodium azide, 0.42 part ammonium chloride, 0.01 part lithium chloride and 9.5 parts dimethylformamide is heated with stirring at about 163° C. (oil bath temperature) for 18 hours under a nitrogen atmosphere. The reaction mixture is cooled to room temperature and the resulting solid precipitate is filtered, washed, and air-dried to afford 5-[1,1-diphenyl-3-(exo-5-hydroxy-2-azabicyclo[2.2.2]oct-2-yl)propyl]-1H-tetrazole. This compound melts at about 285°–286° C. with gas evolution and is represented by the following structural formula.

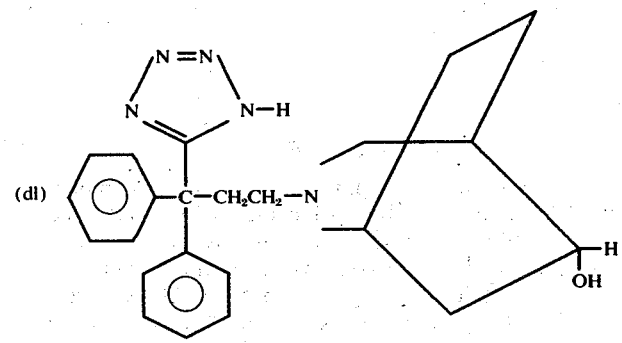

EXAMPLE 18

0.53 Part of 5-[1,1-diphenyl-3-(exo-5-hydroxy-2-azabicyclo[2.2.2]oct-2-yl)propyl]1H-tetrazole is suspended in a solution of 2.3 parts by volume acetic anhydride in 5 parts dry pyridine and the suspension refluxed for approximately two hours under a nitrogen atmosphere. After cooling, the solvents are removed in vacuo. The residual gum is dissolved in water, strongly basified with aqueous potassium carbonate, saturated with sodium chloride and extracted four times with portions of ethyl ether. The ethereal extracts are combined, dried over anhydrous sodium sulfate and stripped in vacuo to afford, as brown gum, 5-[1,1-diphenyl-3-(exo-5-acetoxy-2-azabicyclo[2.2.2]-oct-2-yl)propyl]-2-methyl-1,3,4-oxadiazole. This compound is represented by the following structural formula.

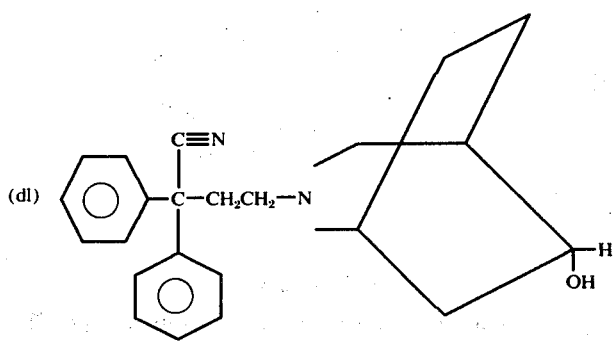

EXAMPLE 17

A solution of 2.0 parts 2,2-diphenyl-4-(exo-5-hydroxy-2-azabicyclo[2.2.2]oct-2-yl)butyronitrile,

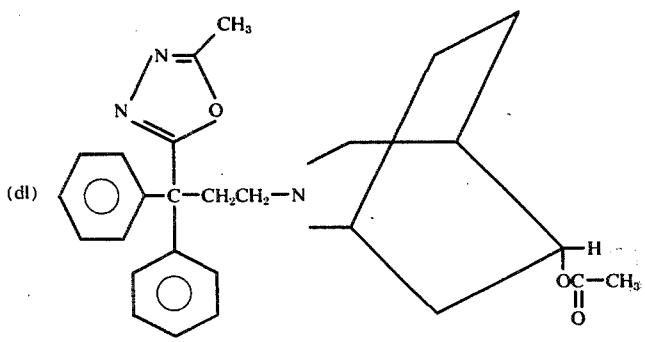

EXMPLE 19

0.57 Part of 5-[1,1-diphenyl-3-(exo-5-acetoxy-2-azabicyclo[2.2.2]oct-2-yl)propyl]-2-methyl-1,3,4-oxadiazole is dissolved in 15 parts methanol, diluted with 8 parts by volume of a 20% sodium hydroxide solution and cooled for 48 hours. The solvents are then stripped in vacuo and the resulting gum partitioned between water and ether five times. The ether extracts are combined, dried over anhydrous sodium sulfate, and reduced in volume in vacuo to about 30 ml. Cooling of this solution results in a white crystalline precipitate which is filtered, washed with ethyl ether, and dried to afford 5-[1,1-diphenyl-3-(exo-5-hydroxy-2-azabicyclo[2.2.2]-oct-2-yl)propyl]-2-methyl-1,3,4-oxadiazole. This compound melts at about 123°–125° C. and is represented by the following structural formula.

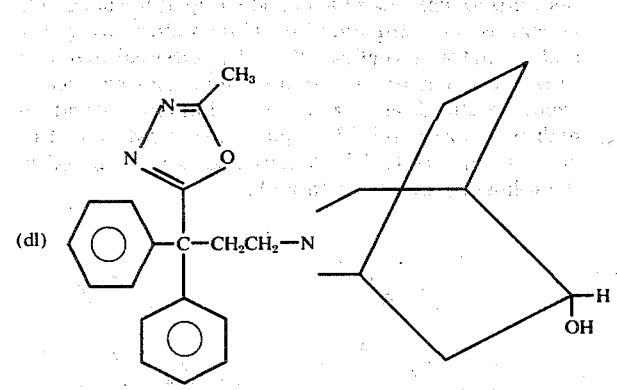

EXAMPLE 20

Repetition of the procedure detailed in the first paragraph of Example 16 using an equivalent quantity of endo2-azabicyclo[2.2.2.]octan-5-ol hydrochloride in place of the exo-2-azabicyclo[2.2.2]octan-5-ol hydrochloride affords 2,2-diphenyl-4-(endo-5-hydroxy-2-azabicyclo[2.2.2]oct-2-yl)butyronitrile hydrochloride, as a tan solid melting at about 200°–203° C.

The free base of this compound, i.e., 2,2-diphenyl-4-(endo-5-hydroxy-2-azabicyclo[2.2.2]oct-2-yl)butyronitrile, is obtained in the same manner as detailed in the second paragraph of Example 6.

EXAMPLE 21

Using an equivalent quantity of 2,2-diphenyl-4-(endo-5-hydroxy-2-azabicyclo[2.2.2]oct-2-yl)butyronitrile, the procedure of Example 17 is repeated to afford 5-[1,1-diphenyl-3-(endo-5-hydroxy-2-azabicyclo[2.2.2]oct-2yl)-propyl]-1H-tetrazole melting at about 294°–295° C. with gas evolution.

EXAMPLE 22

When an equivalent quantity of 5-[1,1-diphenyl-3-(endo-5-hydroxy-2-azabicyclo[2.2.2]oct-2-yl)propyl]-1H-tetrazole is substituted for the 5-[1,1-diphenyl-3-(exo-5-hydroxy-2-azabicyclo[2.2.2]oct-2-yl) propyl]-1H-tetrazole of Example 18, and the procedure detailed therein substantially repeated, there is obtained 5-[1,1-diphenyl-3-(endo-5acetoxy-2-azabicyclo[2.2.2]oct-2-yl)propyl]-2-methyl-1,3,4-oxadiazole melting at about 147°–149° C. after recrystallization from ethyl ether.

EXAMPLE 23

0.18 Part of 5-[1,1-diphenyl-3-(endo-5-acetoxy-2-azabicyclo[2.2.2]oct-2-yl)propyl]2-methyl-1,3,4-oxadiazole is dissolved in 5 parts of boiling methanol. After cooling in an ice-bath, 2.1 parts by volume of a 20% sodium hydroxide solution is added and the mixture allowed to stand for 15.5 hours at room temperature. The resultant crystals are then filtered, washed with methanol and dried in vacuo to afford white needles. Recrystallization from ethyl ether yields 5-[1,1-diphenyl-3-(endo-5-hydroxy-2-azabicyclo[2.2.2]oct-2-yl)-propyl]-2-methyl-1,3,4-oxadiazole melting at about 105.5°–108° C. This compound is represented by the following structural formula.

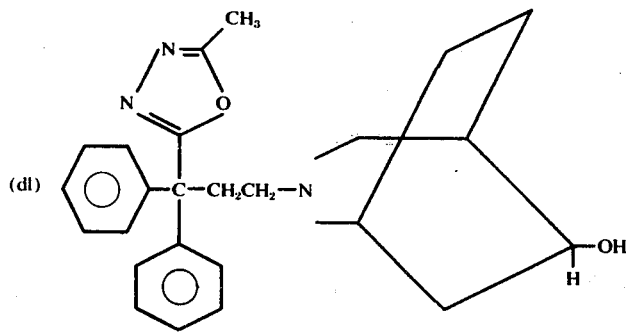

(dl)

EXAMPLE 24

A solution of 21.0 parts 2,2-diphenyl-4-bromobutyronitrile and 8.9 parts endo-2-azabicyclo[2.2.2]oct-6-ol in 55 parts dimethylsulfoxide is heated on a steam bath for about 16 hours. Then, the solution is cooled, poured over chipped ice and water, strongly basified with aqueous sodium hydroxide, and extracted with methylene chloride. The methylene chloride extract is dried over anhydrous sodium sulfate and stripped in vacuo to give a brown gum. The gum is dissolved in ether and the insoluble material removed by filtration. The filtrate is then treated with a solution of hydrogen chloride in isopropanol. The resultant precipitate is filtered, washed, and air dried to yield an off-white solid. Recrystallization of this solid from an ethanol-ether mixture affords 2,2-diphenyl-4-(endo-6-hydroxy-2-azabicyclo[2.2.2]oct-2-yl)butyronitrile hydrochloride hemihydrate. This compound melts at about 181°–184° C. and is represented by the following structural formula.

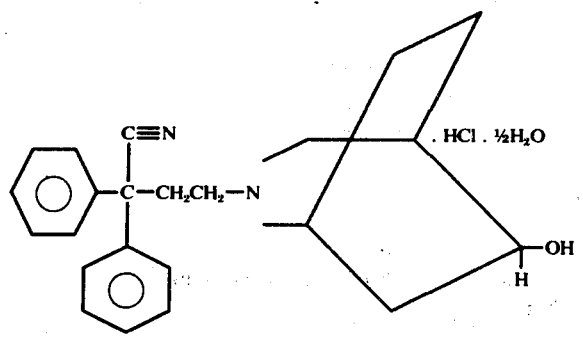

Treatment of the above hydrochloride salt with aqueous sodium hydroxide, followed by extraction into ethyl ether and stripping of the solvents in vacuo affords the free base, 2,2-diphenyl-4-(endo-6-hydroxy-2-azabicyclo[2.2.2]oct-2-yl)butyronitrile.

EXAMPLE 25

Substitution of an equivalent quantity of 2,2-diphenyl-4-(endo-6-hydroxy-2-azabicyclo[2.2.2]oct-2-yl)butyronitrile in the procedure of Example 17 affords 5-[1,1-diphenyl-3-(endo-6-hydroxy-2-azabicyclo[2.2.2]oct-2-yl)propyl]-1H-tetrazole. This compound melts at about 277°–278° C. with gas evolution.

EXAMPLE 26

When an equivalent quantity of 5-[1,1-diphenyl-3-(endo-6-hydroxy-2-azabicyclo[2.2.2]oct-2-yl)propyl]-1H-tetrazole is substituted for the 5-[1,1-diphenyl-3-(exo-5-hydroxy-2-azabicyclo[2.2.2]oct-2-yl)propyl]-1H-tetrazole of Example 18, and the procedure detailed therein substantially repeated, there is obtained, as a gum, 5-[1,1-diphenyl-3-(endo-6-acetoxy-2-azabicyclo[2.2.2]oct-2-yl)propyl]-2-methyl-1,3,4-oxadiazole.

EXAMPLE 27

0.10 Part of 5-[1,1-diphenyl-3-(endo-6-acetoxy-2-azabicyclo[2.2.2]oct-2yl)propyl]-2-methyl-1,3,4-oxadiazole is dissolved in 5 parts methanol and treated with 1.5 parts by volume of a 20% sodium hydroxide solution. After standing for 11 days, the solution is neutralized with acetic acid and stripped in vacuo. The residue is then suspended in dilute sodium hydroxide and extracted into ethyl ether. The ethereal extract is dried over anhydrous sodium sulfate and stripped in vacuo to afford, as a gum, 5-[1,1-diphenyl-3-(endo-6-hydroxy-2-azabicyclo[2.2.2]oct-2-yl)propyl]-2-methyl-1,3,4-oxadiazole. This compound is represented by the following structural formula.

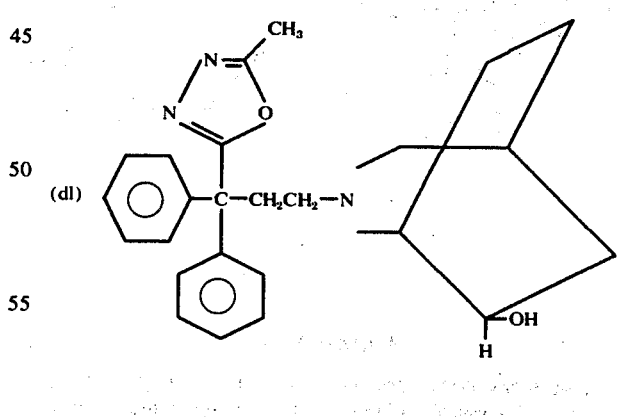

(dl)

EXAMPLE 28

Repetition of the procedure detailed in the first paragraph of Example 24 using an equivalent quantity of exo-2-azabicyclo[2.2.2]octan-6-ol in place of the endo-2-azabicyclo[2.2.2]oct-6-ol affords 2,2-diphenyl-4-(exo-6-hydroxy-2-azabicyclo[2.2.2]oct-2-yl)butyronitrile hydrochloride.

The free base of this compound is obtained in the same manner in the second paragraph of Example 24.

EXAMPLE 29

Using an equivalent quantity of 2,2-diphenyl-4-(exo-6-hydroxy-2-azabicyclo[2.2.2]oct-2-yl)butyronitrile, the procedure of Example 17 is repeated to yield 5-[1,1-diphenyl-3-[exo-6-hydroxy-2-azabicyclo[2.2.2]oct-2-yl)propyl]-1H-tetrazole.

EXAMPLE 30

When an equivalent quantity of 5-[1,1-diphenyl-3-[exo-6-hydroxy-2-azabicyclo[2.2.2]oct-2-yl)propyl]-1H-tetrazole is substituted for the 5-[1,1-diphenyl-3-[exo-5-hydroxy-2-azabicyclo[2.2.2]oct-2-yl)propyl]-1H-tetrazole of Example 18, and the procedure detailed therein substantially repeated, there is obtained 5-[1,1-diphenyl-3-(exo-6-acetoxy-2-azabicyclo[2.2.2]oct-2-yl)propyl]-2-methyl-1,3,4-oxadiazole.

EXAMPLE 31

Repetition of the procedure of Example 27 using 5-[1,1-diphenyl-3-(exo-6-acetoxy-2-azabicyclo[2.2.2]oct-2-yl)-propyl]-2-methyl-1,3,4-oxadiazole affords 5-[1,1-diphenyl-3-(exo-6-hydroxy-2-azabicyclo[2.2.2]oct-2-yl)propyl]-2-methyl-1,3,4-oxadiazole. This compound is represented by the following structural formula.

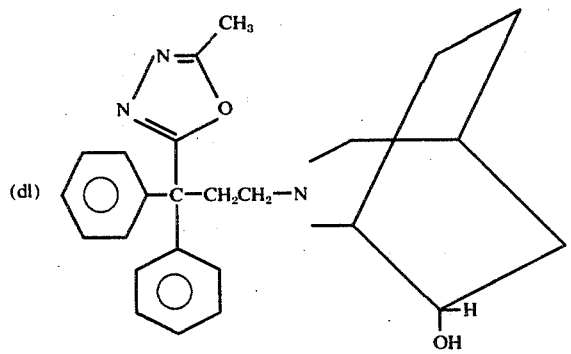

What is claimed is:

1. A compound of the formula

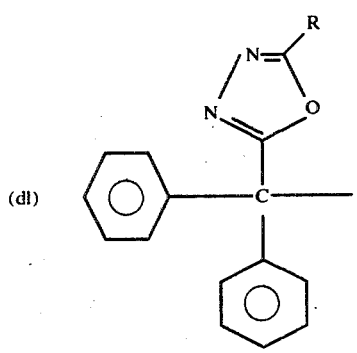

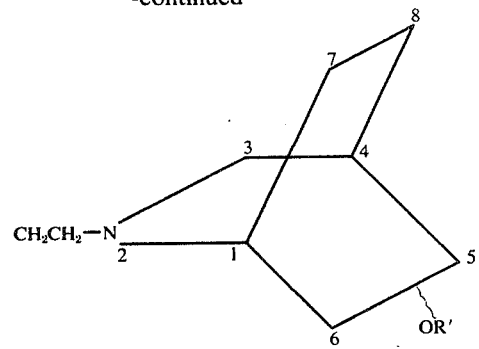

wherein R is lower alkyl containing from 1 to 6 carbon atoms; R' is hydrogen or a lower alkanoyl containing from 2 to 7 carbon atoms; and OR' is attached at the 5- or 6-position in either the endo or exo configuration.

2. A compound according to claim 1 of the formula

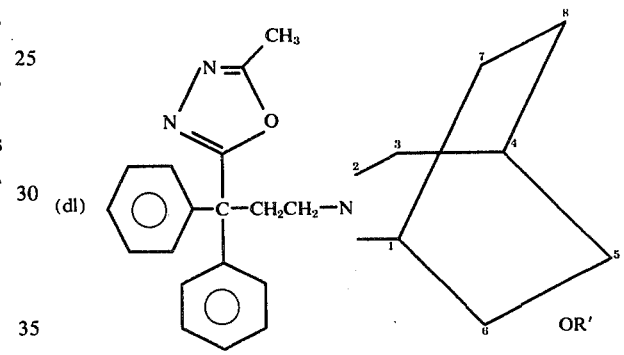

wherein R' is hydrogen or acetyl and OR' is attached at the 5- or 6-position in either the endo or exo configuration.

3. The compound according to claim 1 which is 5-[1,1-diphenyl-3-(exo-5-hydroxy-2-azabicyclo[2.2.2]oct-2-yl)-propyl]-2-methyl-1,3,4-oxadiazole.

4. The compound according to claim 1 which is 5-[1,1-diphenyl-3-(exo-5-acetoxy-2-azabicyclo[2.2.2]oct-2-yl)-propyl]-2-methyl-1,3,4-oxadiazole.

5. The compound according to claim 1 which is 5-[1,1-diphenyl-3-(endo-5-acetoxy-2-azabicyclo[2.2.2]oct-2-yl)-propyl]-2-methyl-1,3,4-oxadiazole.

6. The compound according to claim 1 which is 5-[1,1-diphenyl-3-(endo-5-hydroxy-2-azabicyclo[2.2.2]oct-2-yl)-propyl]-2-methyl-1,3,4-oxadiazole.

7. The compound according to claim 1 which is 5-[1,1-diphenyl-3-(endo-6-acetoxy-2-azabicyclo[2.2.2]oct-2-yl)-propyl]-2-methyl-1,3,4-oxadiazole.

8. The compound according to claim 1 which is 5-[1,1-diphenyl-3-(endo-6-hydroxy-2-azabicyclo[2.2.2]oct-2-yl)-propyl]-2-methyl-1,3,4-oxadiazole.

9. The compound according to claim 1 which is 5-[1,1-diphenyl-3-(exo-6-acetoxy-2-azabicyclo[2.2.2]oct-2-yl)-propyl]-2-methyl-1,3,4-oxadiazole.

10. The compound according to claim 1 which is 5-[1,1-diphenyl-3-(exo-6-hydroxy-2-azabicyclo[2.2.2]oct-2-yl)-propyl]-2-methyl-1,3,4-oxadiazole.

* * * * *

UNITED STATES PATENT AND TRADEMARK OFFICE
CERTIFICATE OF CORRECTION

PATENT NO. : 4,013,668
DATED : March 22, 1977
INVENTOR(S) : Gilbert W. Adelstein, Aziz Karim, Chung H. Yen It is certified that error appears in the above-identified patent and that said Letters Patent are hereby corrected as shown below:

Column 1, line 30, "OR'" should be --〜〜OR'--.

Column 3, line 20, "the should be -- then --.

Column 14, line 15, "210°" should be -- 201° --.

Column 22, Cl. 1, line 18, "OR'" should be --〜〜OR'--.

Column 22, Cl. 2, line 38, "OR'" should be --〜〜OR'--.

Column 22, Cl. 2, formula, in part,

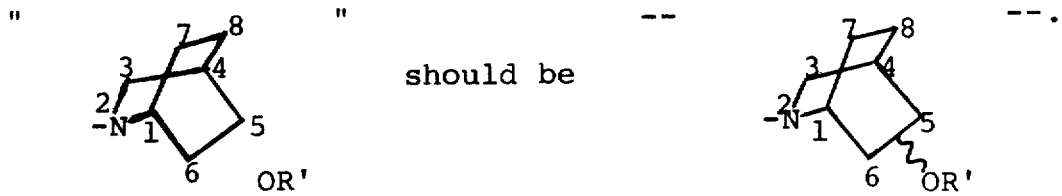

Signed and Sealed this

Fifteenth Day of August 1978

[SEAL]

Attest:

RUTH C. MASON
Attesting Officer

DONALD W. BANNER
Commissioner of Patents and Trademarks